United States Patent [19]

Stegink et al.

[11] Patent Number: 5,296,637
[45] Date of Patent: Mar. 22, 1994

[54] PRODUCTION OF ODOR-FREE TETRAHYDROISOHUMULATES FROM ALPHA ACIDS VIA THEIR TETRAHYDROHUMULATES AND SUBSEQUENT ISOMERIZATION

[75] Inventors: Larry J. Stegink; James A. Guzinski; Paul H. Todd, Jr., Kalamazoo, all of Mich.

[73] Assignee: Kalamazoo Holdings, Inc., Kalamazoo, Mich.

[21] Appl. No.: 999,599

[22] Filed: Dec. 31, 1992

[51] Int. Cl.$^5$ .............................................. C07C 45/67
[52] U.S. Cl. ................................... 568/341; 568/347; 426/600
[58] Field of Search ................ 568/347, 341; 426/600; 508/347, 341

[56] References Cited

U.S. PATENT DOCUMENTS

| | | | |
|---|---|---|---|
| 3,923,897 | 12/1975 | Worden | 568/341 |
| 4,007,683 | 1/1977 | Todd | 568/341 |
| 4,234,516 | 11/1980 | Koller et al. | 568/341 |
| 4,247,483 | 1/1981 | Baker et al. | 568/341 |
| 4,666,731 | 5/1987 | Todd | 426/600 |
| 4,778,691 | 10/1988 | Todd | 426/600 |
| 5,013,571 | 5/1991 | Hay | 426/600 |
| 5,013,572 | 5/1991 | Hay | 426/600 |

OTHER PUBLICATIONS

Verzele and De Keukeleire, "Chemistry and Analysis of Hop and Beer Bitter Acids", Developments in Food Science 27, by Elsevier Publishing House, New York (1991), cover page, two page Preface, two page Table of Contents, pages 19-21 and 44-46 from Chapter 3 entitled Reduced derivatives of humulone.
Verzele, et al., "On The Hydrogenation Of Humulone Part I. The Preparation of Tetrahydrohumulone", Bull. Soc. Chim. Belg., 68, Jul. 15, 1959, pp. 315-324.
Anteunis, et al., "On The Hydrogenation Of Humulone Part II. The Mechanism of the Hydrogenolysis", Bull. Soc. Chim. Belg., 68, Sep. 15, 1959, pp. 476-483.

*Primary Examiner*—James H. Reamer
*Attorney, Agent, or Firm*—Gordon W. Hueschen

[57] ABSTRACT

The present application discloses a novel and advantageous method for the preparation of essentially odor-free alkali metal tetrahydroisohumulate (THIH) which proceeds through isomerization of the essential alkali metal tetrahydrohumulate (THH) intermediate, which is in turn produced by the hydrogenation with two moles of hydrogen of a starting alkali metal humulate (H) at a pH of at least 10, the intermediate THH being thus produced with relative ease and in high yields and purity, which high yields and purity carry over to the ultimate end product, namely, to the essentially aroma-, odor-, and impurity-free THIH, which end product accordingly does not require steam-stripping or other cleanup procedure as is conventional for THIH produced from other sources or by other procedure.

11 Claims, No Drawings

PRODUCTION OF ODOR-FREE TETRAHYDROISOHUMULATES FROM ALPHA ACIDS VIA THEIR TETRAHYDROHUMULATES AND SUBSEQUENT ISOMERIZATION

FIELD OF INVENTION

Production of odor-free alkali metal tetrahydroisohumulates by isomerization of alkali metal tetrahydrohumulates produced by hydrogenation of alpha acids in the form of their alkali metal humulates.

BACKGROUND OF INVENTION AND PRIOR ART

Alpha acids (or humulones) have the formula AA:

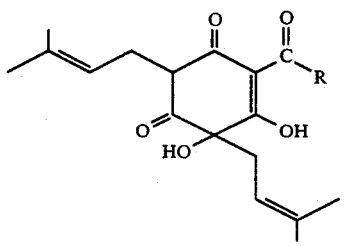

wherein R is isopropyl, isobutyl, or secondary butyl.

Alkali metal humulates have the formula H:

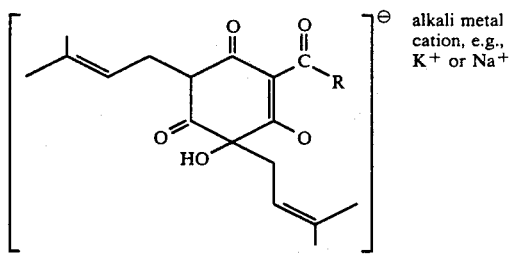

Alkali metal tetrahydrohumulates have the formula THH:

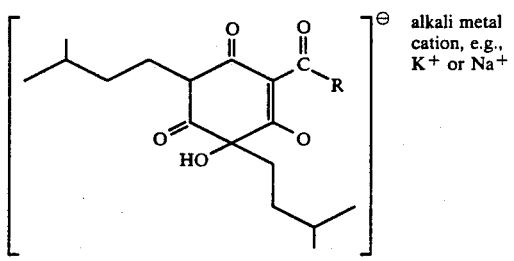

Tetrahydroalpha acids (or tetrahydrohumulones) have the formula THAA:

Isoalpha acids (or isohumulones) have the formula IAA:

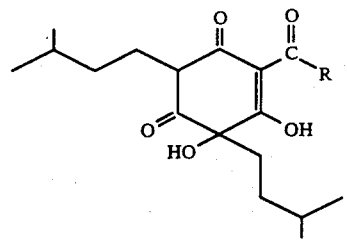

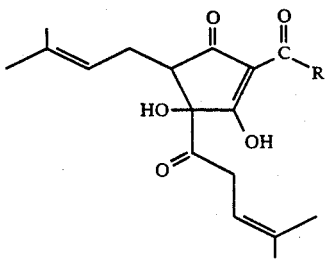

and are not involved according to the present invention.

Tetrahydroisoalpha acids (or tetrahydroisohumulones) have the formula THIAA:

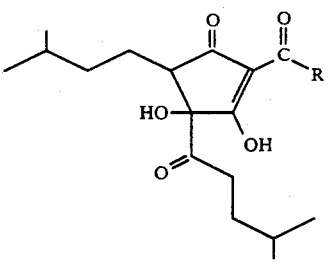

Tetrahydroisohumulates have the formula THIH:

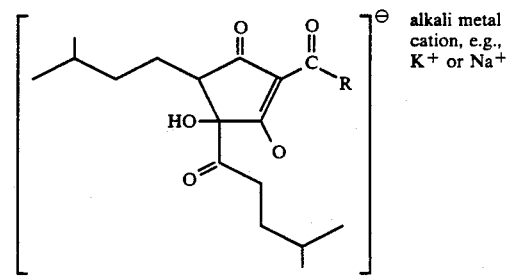

it being recognized that keto-enol tautomerism exists.

Isohumulates have the formula IH:

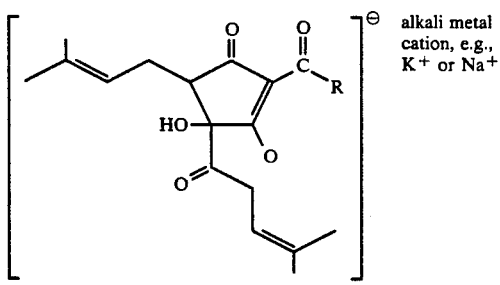
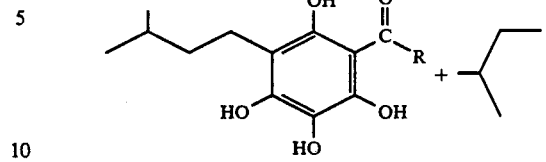

and are not involved according to the present invention.

The bitterness of beer is due to the presence of isoalpha acids, which are currently used in both their reduced and unreduced forms, and ordinarily in the form of an isohumulate or reduced isohumulate. The unreduced form is made by isomerization by boiling of the alpha acids naturally present in hops, or by catalytic isomerization utilizing magnesium or calcium ions, all as well known in the art. Tetrahydroisoalpha acids or salts thereof have been made by oxidative conversion of beta acids to tetrahydroalpha acids (Worden U.S. Pat. No. 3,923,897), and isomerization of these hydrogenated alpha acids to tetrahydroisoalpha acids. More recently Hay (U.S. Pat. No. 5,013,571) has described a process for the "simultaneous" catalytic isomerization and hydrogenation of isoalpha acids to tetrahydroisoalpha acids, as well as the hydrogenation of previously-isomerized isoalpha acids. Hay (U.S. Pat. Nos. 5,013,571 and 5,013,572) has also described a method of steam stripping unwanted estery aromas from the hydrogenated isoalpha acids produced by his process.

Todd (U.S. Pat. No. 4,778,691) describes the separation of unwanted impurities into an aqueous phase from an organic phase of unreduced and/or reduced alpha and isoalpha acids. Todd (U.S. Pat. No. 4,647,464) describes the separation of alpha and beta acids from a carbon dioxide hop extract, providing an alpha acid fraction which is essentially devoid of impurities and which may be isomerized by heat alone to isoalpha acids without the formation of isomerization by-products, by using less than one mole of base per mole of alpha acid in the separation step. Such an alpha acid fraction is an excellent starting material for use according to the present invention.

The general background of the art is well described in the foregoing series of patents. Worden shows that tetrahydroalpha acids can be made from beta acids and then isomerized to tetrahydroisoalpha acids. Alternatively, alpha acids are isomerized to isoalpha acids, which in turn are hydrogenated, as shown by Hay, even when the two successive steps are carried out in the same medium (Hay, '571, Col. 2, lines 33-37, and confirmed in Example 9 hereof).

The art has not been able to utilize alpha acids as a source of tetrahydrohumulates, with subsequent isomerization to tetrahydroisohumulates. Verzele, (Bulletin des Societes Chimiques Belges 68. pp 315-324 and 476-583 (1959)) found that, upon hydrogenation of alpha acids at a pH up to 8.1 on the alkaline side, substantial amounts of quinone formation occurred. Verzele used a minimum of 2.2 moles of hydrogen per mole of alpha acids, which also resulted in perhydrogenation or over-reduction under his conditions. This may be attributed to the partial hydrogenation of keto groups on the alpha acid molecule. The formation of humuloquinones HQ:

depends upon the presence of the six-membered ring present in alpha acids, and they (HQ) cannot be formed from a compound having the five-membered ring of the iso acids. This is why Hay could produce tetrahydroisoalpha acids by hydrogenation of isoalpha acids without quinone formation, even though he employed hydrogen pressures of up to 2,000 psig and a pH as low as 5 to 7 (Hay '571, Col. 9).

OBJECTS OF THE INVENTION

It is an object of the invention to provide a process for the preparation of an alkali metal tetrahydrohumulate in high yield and purity which consists essentially of the step of hydrogenating with two moles of hydrogen and in the presence of a noble metal catalyst a solution of an alkali metal humulate at a pH of at least 10 to produce an alkali metal tetrahydrohumulate, the important intermediate alkali metal tetrahydrohumulate in solution at a pH of at least 10 in the presence of a noble metal catalyst and optionally buffered at such pH, and such a composition wherein the metal is sodium or potassium; the solvent is a lower-alkanol, water, or a combination thereof; the pH is 10.5 to 12 and optionally buffered at such pH.

A particular object is the provision of a process for the preparation of essentially odor- and aroma-free alkali metal tetrahydroisohumulates of high purity and in high yield which consists essentially of the steps of hydrogenating with two moles of hydrogen and in the presence of a noble metal catalyst a solution of an alkali metal humulate at a pH of at least 10 to produce an alkali metal tetrahydrohumulate and isomerizing the thus-produced alkali metal tetrahydrohumulate to alkali metal tetrahydroisohumulate, and essentially estery or fruity odor- and aroma-free alkali metal tetrahydroisohumulate produced by said process.

Further objects of the invention will become apparent hereinafter and still others will be obvious to one skilled in the art to which this invention pertains.

SUMMARY OF THE INVENTION

The invention, then, comprises the following, inter alia singly or in combination:

A process for the preparation of an alkali metal tetrahydrohumulate in high yield and purity which consists essentially of the step of hydrogenating with two moles of hydrogen and in the presence of a noble metal catalyst a solution of an alkali metal humulate at a pH of at least 10 to produce an alkali metal tetrahydrohumulate; such a process wherein the alkali metal is sodium or potassium; the solvent is a lower-alkanol, water, or a combination thereof; the pH is 10.5 to 12 and optionally buffered at such pH; such a process wherein the noble metal catalyst is palladium on charcoal; and the important intermediate composition consisting essentially of an alkali metal tetrahydrohumulate in solution at a pH of at least 10 in the presence of a noble metal catalyst and optionally buffered at such pH; and such a composition wherein the alkali metal is sodium or potassium; the solvent is a lower-alkanol, water, or a combination thereof; the pH is 10.5 to 12 and optionally buffered at such pH.

Also, a process for the preparation of essentially estery or fruity odor- and aroma-free alkali metal tetrahydroisohumulate of high purity and in high yield which consists essentially of the steps of hydrogenating with two moles of hydrogen and in the presence of a noble metal catalyst a solution of an alkali metal humulate at a pH of at least 10 to produce an alkali metal tetrahydrohumulate (as described in the foregoing), and isomerizing under isomerization conditions the thus-produced alkali metal tetrahydrohumulate to alkali metal tetrahydroisohumulate; such a process wherein the alkali metal is sodium or potassium; the solvent is a lower-alkanol, water, or a combination thereof; the pH is 10.5 to 12 and optionally buffered at such pH; such a process wherein the noble metal catalyst is palladium on charcoal; such a process wherein the isomerization is effected by boiling or catalytically using calcium or magnesium ions; and the important end product essentially estery or fruity odor- and aroma-free alkali metal tetrahydroisohumulate produced by the said process.

GENERAL DESCRIPTION OF THE PRESENT INVENTION

The present invention involves an improvement in the art whereby alpha acids are used as the starting material for alkali metal tetrahydrohumulates, rather than beta acids, and hydrogenated in the form of their alkali metal humulates, the tetrahydrohumulates thereafter advantageously being isomerized to tetrahydroisohumulates if desired.

Contrary to Verzele, who shows the reduction of alpha acids leading to unwanted by-product formation, it is found that, when alkali metal salts of alpha acids (called humulates) are hydrogenated, by-products including humuloquinones are eliminated, and perhydrogenation does not occur. Surprisingly also, under-reduction does not occur with the formation of less-desirable dihydroalpha acids (which form light-unstable product when isomerized), which dihydro compounds were also found in Verzele's reaction product even though he used an excess of hydrogen. Furthermore, the undesirable estery aromas, produced during the hydrogenation of isoalpha acids to tetrahydroisoalpha acids according to Hay, are not formed, and steam-stripping to remove these, as described in his patents, is therefore not required, even when alcohols such as methanol, ethanol, and isopropanol are employed in the reaction medium, quite in contrast to Hay '572, Col. 2, lines 47-56.

Because the hydrogenation of the present invention starting from an alkali metal humulate automatically stops, for reasons unknown and unexpected, at an uptake of two moles, the perhydrogenation which occurs when hydrogenating isoalpha acids (cf. Example 4 hereof) as well as when hydrogenating alpha acids under the conditions of Verzele, does not take place. All of these advantages combine to make the hydrogenation of humulates with two moles of hydrogen according to the present invention a significant advance in the art, especially when taken together with the subsequent isomerization step (starting from tetrahydrohumulates) to the ultimately-desired tetrahydroisohumulates. Thus, by hydrogenating the humulate H with two moles of hydrogen to the tetrahydrohumulate THH, in which reaction the uptake of hydrogen automatically stops at the desired two (2) moles, without any under-reduction or perhydro or humuloquinone HQ contaminants, and then isomerizing the tetrahydrohumulate THH to the tetrahydroisohumulate THIH, a most desirable THIH end product is produced, which is devoid of undesirable estery or fruity odors or aromas, in high purity and without any humulinic acid HA, apparently due to the fact that it is the THH which is being isomerized and not the isohumulate IH which is being hydrogenated, as in Hay.

Following hydrogenation of the alkali metal humulate, which may also be described as a humulate anion combined with an alkali metal cation, to produce the corresponding tetrahydrohumulate, the tetrahydrohumulate may be readily recovered and isomerized by methods well known to the art (e.g., Worden), such as by boiling or catalytically using Ca or Mg ions. Such isomerized alkali metal tetrahydroisohumulates have two significant and unexpected advantages over the tetrahydroisoalpha obtained by the direct hydrogenation of isoalpha acids: (1) the estery aromas of Hay do not form, do not require removal by steam stripping or otherwise, and do not "reform" after standing; (2) less than about two or three percent of by-products are formed in the hydrogenation and subsequent isomerization, under readily-achieved commercial conditions, thereby avoiding the necessity of a costly "clean-up" by the method of Todd. Expected undesirable reaction by-products, including humulinic acid, humuloquinones, and partially-reduced and over-reduced alpha acids, and undesirable aromas or odors are not a product of the present inventive process.

The hydrogenation medium is preferably either an aqueous or aqueous/lower alkanol medium, although less protic solvents, such as ethyl acetate, may be used. The preferred catalyst is palladium on charcoal, but other noble metals such as platinum and rhodium may be employed. The alkali metal cation of the humulate is preferably potassium or sodium. Hydrogenation temperature and pressure ranges can be adapted to the equipment available. For practical reasons, temperatures between about 20° C. and 40° C., and pressures between 10 and 50 lbs. psi, are preferred.

Critical to the invention is the necessity of having more than one mole of cation per mole of anion, as essentially none of the alpha acids can be in their free acid form if the present inventive process is to be fully successful. This means that the pH of the reducing medium must be at least about 10, preferably above about 10.5, and optimally 10.5 to 12. Higher ranges of pH may be employed, but serve no useful purpose. It should be noted that, at these pH ranges, alpha acids normally isomerize to isoalpha acids and degrade to humulinic acids as is well known to the art. Surprisingly, neither reaction takes place under the present hydrogenation conditions. Humulinic acids (HA)

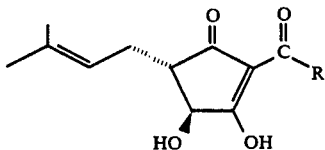

are not formed as would be the case if isoacids were present or produced in the process.

Purity Measurements

HPLC is an accepted method of determining the presence of reaction by-products in isoalpha and tetrahydroisoalpha acids, as well as in alpha acids, as well as their salts. The acids or acid salts are separated from the impurities, and the relative amounts thereof are measured as an area count at a specific wavelength. The yield may be determined by this method: alpha or isoalpha acids of known HPLC purity are converted to their tetrahydro potassium salt derivative, and the area count of desired product as a % of the total area count is an excellent estimate of the yield.

Undesirable perhydrogenation may be detected by the ratio of the absorbance at 254 nm to that at 270 nm in alkaline methanol. A ratio of between 1.15 and 1.21 is typical of sodium or potassium tetrahydroisohumulate which has not been perhydrogenated, whereas a ratio below about 1.14 shows perhydrogenation.

SPECIFIC DESCRIPTION OF THE INVENTION

The following Examples are given to illustrate the present invention, but are not to be construed as limiting.

The Examples show (1) the critical lower limit of pH 10 required to achieve production of the desired tetrahydrohumulate, (2) the suitability of a pH above this lower limit, (3) the freedom from any non-volatile or volatile by-products produced during the hydrogenation, (4) the essentially quantitative yield under the critical conditions, (5) subsequent isomerization and storage of isohumulate product, and (6) the absence of objectionable odoriferous by-products in the isohumulate product obtained. A comparison with the product of the prior art tetrahydroisoalpha acid product made via hydrogenation of beta acids or of isoalpha acids is also provided.

Example 1 shows a preferred method for the hydrogenation of humulate and subsequent isomerization, and compares the product with commercial product made from (1) hydrogenated isoalpha acids and (2) beta acids. The purity of the tetrahydroalpha acids is the same as the starting alpha acids, 94%, and the isomerized product, tetrahydroisoalpha acids, are 92% pure. This compares with 93% purity for commercial product from beta acids, recovered following the clean-up procedure of Todd, and 81% purity for commercial product made by hydrogenation of isoalpha acids. The tetrahydrogenated product of the present invention may be simply recovered, following removal of catalyst, before or after isomerization, by procedure well known to the art.

In Example 1 of U.S. Pat. No. 4,666,731, it is shown that slightly less than one equivalent of base (0.94E) to alpha acid results in a pH of about 8.6. Example 2 hereof shows that, at a pH of 9.5, the level of impurities produced by the hydrogenation is unacceptable. More than one equivalent of base is required to achieve desirable purities and yields, and this is critical to the hydrogenation step of the present invention. All alpha acid must be converted to humulate ion prior to hydrogenation. More than one equivalent of base results in a pH above about 10, this being the lower practical limit for the present hydrogenation process. The criticality is shown by Example 2.

Hay shows the "simultaneous" isomerization and hydrogenation of alpha acids in his examples and claims. He believes that isomerization precedes hydrogenation. Example 9 hereof validates his belief, confirming that he hydrogenates preformed isoalpha acids rather than alpha acids or humulates. It is of course nowhere suggested that the hydrogenation of iso (according to Hay) proceeds much more slowly, even 100% more slowly, than the hydrogenation of humulate (according to the present invention) even at ambient temperatures, as we have found to be the case. The relative ease and a quantitative theoretical uptake of two moles of hydrogen in the hydrogenation step of the present invention is a further unpredictable benefit offered thereby.

EXAMPLE 1

Measurement of purity and reaction by-products, including perhydrogenation.

A comparison of the spectral ratios and HPLC purities of commercial tetrahydroisoalpha acids, as well as the same product produced according to the present invention in each case in the form of their potassium salts, or isohumulates, are portrayed in Table I below, which depicts the various products made according to procedures (A), (B), and (C):

(A) A preferred procedure. 20 g of alpha acids were converted to potassium humulate by addition to a medium containing 100 ml methanol and 5 ml 45% aqueous KOH. It is advantageous, but not essential, to use aqueous KOH. There were about 1.1-1.2 equivalents of potassium ion present, and the pH was 11.9. 20% by weight of 5% palladium on charcoal was added, and the medium was hydrogenated using a Parr shaker at ambient temperature and 40 lbs. psi hydrogen pressure until uptake of two moles of hydrogen ceased, which took about three hours. The analysis of this product is shown in Table I.

(B) The tetrahydro humulate of (A) was converted to potassium tetrahydroisohumulate by boiling in water, during which time any residual methanol was removed by vaporization. Analysis is also provided in Table 1. Product was diluted with water to a 10% concentration.

(C) HPLC purity and the 254/270 absorbance ratios of 10% aqueous solutions of commercial tetrahydroisoalpha acids produced from beta acids and by hydrogenation of isoalpha acids were compared, and the results are also shown in Table 1.

TABLE 1

| Comparative purities of tetrahydroalpha and isoalpha acids. ((A) and (B) are from Example 1) | | | |
|---|---|---|---|
| | HPLC % purity | ratio 270/254 | estery aroma present |
| (A) alpha acids | 93.8 | not applicable | none |
| potassium tetrahydrohumulate | 94 | | none |
| (B) potassium tetrahydroisohumulate from potassium | 92 | 1.18 | none |

TABLE 1-continued

Comparative purities of tetrahydroalpha and isoalpha acids.
((A) and (B) are from Example 1)

|  | HPLC % purity | ratio 270/254 | estery aroma present |
|---|---|---|---|
| (C) tetrahydrohumulate commercial potassium tetrahydroisohumulate from beta | 93 | 1.18 | yes, weak |
| commercial potassium tetrahydroisohumulate from iso | 81 | 1.04 | yes, strong |

This comparative example, in which the comparison is made in each case in the form of the potassium salt, shows that the tetrahydroisoalpha acids made from alpha acids via humulates according to the present invention is far superior in purity to that made from isoalpha acids, that the yield is superior by ca. 11%, that perhydrogenation did not occur, and that estery aromas are not produced and do not form on standing. No humulinic acid or dihydro product was detected by HPLC. The purity of the iso product of the present invention compares favorably with that of commercial material made from beta acids, without the presence of estery aromas which must be removed.

EXAMPLE 2

Optimal pH Ranges for Hydrogenation of Humulate

Table 2 gives the analysis of potassium tetrahydrohumulate made according to the procedure of (A) in Example 1, and using the same potassium humulate, made from the same alpha acid, which had an HPLC purity of 93.8%. The pH was adjusted by varying the amounts of KOH added to the starting alpha acid.

TABLE 2

Effect of pH on yield and purity.

| pH | HPLC purity | % yield |
|---|---|---|
| 5.0 | 60.4 | impractically low |
| 9.5 | 71.9 | " |
| 9.9 | 83.1 | marginal low |
| 10.1 | 91.1 | 97.1 |
| 10.5 | 91.7 | 97.7 |
| 11.9 | 94.4 | 100 |

This Example shows the criticality of having a pH of at least about 10, and that a pH of approximately 10.5 to 12 is preferred, as precise pH adjustment is not required in this range. A pH as high as 13 or even above is operational. It is best to operate well above the minimum range to escape from meter fluctuation.

The potassium tetrahydrohumulate made at pH 11.9 was isomerized by boiling. The iso product had an HPLC purity of 92% and 254/270 ratio of 1.18. It did not have or develop a fruity aroma, even on standing, and the yield was 97.5%.

This Example demonstrates that the high purity of the product and high yield are maintained through the isomerization step, which is unexpected.

EXAMPLE 3

Use of sodium ion to form sodium humulate

The procedure of Example 1 (A) was followed, except that sodium hydroxide was substituted for potassium hydroxide, and the amount of solvent was doubled. The resulting tetrahydrohumulate was 92.2% pure by HPLC, and the yield was 98.3%. This shows that other alkali metal cations may be used to form the metal humulate along with the humulate anion.

EXAMPLE 4

Absence of perhydrogenation

The procedures of Example 1 (A) and (B) were followed, except that the pH was 11.2, and the hydrogenation was permitted to continue for fifteen hours. The theoretical two moles of hydrogen was taken up within three hours and further uptake did not occur.

The HPLC purity of the potassium tetrahydrohumulate was 91.1%, the yield 97%, the HPLC purity of the tetrahydroisohumulate 91.5%, and the 254/270 ratio 1.15.

In contrast, the drawback of perhydrogenation when isohumulates are subjected to hydrogenation was shown by reducing potassium isohumulate in alkaline (KOH) methanolic solution according to the procedure of Example 1 (A). The temperature was about 38° C. to 45° C., and the hydrogenation, although incomplete, was stopped after five hours. The initial isohumulate had a 254/270 ratio of 1.17, which is essentially the same as the 1.18 ratio of the tetrahydroisohumulate of Example 1 (B). The product of this process, consisting of tetrahydroisohumulate and some unreduced isohumulate, had a ratio of 1.01, typical of perhydrogenated tetrahydroisohumulate, and certainly not typical of the tetrahydroisohumulate made above in this same Example, from deliberately-prolonged hydrogenation of potassium humulate.

This conclusively shows that overhydrogenation does not occur according to the present invention, and that purity and yield are not affected under conditions which would normally result in perhydrogenation, as is the case with hydrogenation of isoalpha acids.

EXAMPLE 5

Buffered hydrogenation medium 20 g of alpha acids, 100 ml of methanol, and 5 ml of 45% KOH were mixed, and 5 g of 5% palladium on charcoal was added. To this mixture, 1.5 g of sodium bicarbonate was added, and the medium became buffered at a pH of 10.4. The mixture was hydrogenated for three hours at ambient temperature and 35 pounds psi pressure. The potassium tetrahydrohumulate product had an HPLC purity of 93.4%, for a yield of 99%.

Other non-reactive buffers, such as phosphates, may be used but are not necessary.

EXAMPLE 6

Use of isopropanol or ethanol as a solvent 20 g of alpha acids, 80 ml of isopropanol, and 5 ml of 45% KOH were mixed and 5 g of 5% palladium on charcoal was added. The pH was 11.6. The potassium humulate-containing mixture was hydrogenated for four hours (uptake of two moles of hydrogen ceased in about three hours) in a Parr shaker at ambient temperature and 35 lbs. psi pressure. The THH product had an HPLC purity of 93% for a yield of 98%.

The same procedure was used, except that ethanol was substituted for isopropanol. The THH product had an HPLC purity of 86.9%.

Aroma test by panel

Both of the above tetrahydrohumulate products of this Example were isomerized by boiling in an aqueous solution at pH 10, as is known in the art for such isomerization. The thus-formed tetrahydroisohumulate products were diluted to a 10% solution in water at a pH of 10 and evaluated for a fruity-estery aroma alongside the potassium tetrahydroisohumulate made in Example 9 by the reduction of isohumulates, as well as a commercial product made from beta acids.

The evaluation of the aromas was made by smelling jars of 10% aqueous solutions using a trained panel. The results were analyzed using the standard statistical tables for triangular tests, as is well recognized in the flavoring art. The potassium tetrahydroisohumulates of this Example 6, made by the reduction of alpha acids in the form of their humulates and subsequent isomerization of the resulting tetrahydrohumulates, did not have an esteryfruity aroma, whereas those of Example 9 and the commercial product, made by the reduction of isohumulate ala Hay and Pfizer, had a definite estery-fruity aroma. These results were at a 95% to 99% confidence level.

EXAMPLE 7

Use of ethyl acetate as a solvent 20.5 g of alpha acids, 80 g of ethyl acetate, and 5 ml of 45% KOH were mixed and 7.5 g of 5% palladium on charcoal added. The mixture was hydrogenated as in Example 6 for three hours. The product had a purity of 89% by HPLC for a yield of 95%.

EXAMPLE 8

Use of water as a solvent 20 g of alpha acids, 80 ml of water, and 5 ml of 45% KOH were mixed. 12.5 g of 5% palladium on charcoal was added and the reaction mixture shaken on a Parr shaker for seven hours at ambient temperature and 35 lbs. psi hydrogen pressure. The potassium tetrahydroisohumulate product had an HPLC purity of 88% and the yield was 94%.

EXAMPLE 9

Comparative rates of isomerization of alpha acids to isoalpha acids, and of hydrogenation of the isoalpha acids 14.5 g of the alpha acids used in Example 1 was dissolved in 35 ml of methylene chloride. To this solution, 35 ml of water was added, then pH adjusted to 10.5 with 45% KOH, 1 g of magnesium chloride added, and the pH readjusted to 10.5. The solution was agitated at 38° C. in a Parr shaker under 40 psi hydrogen pressure. Samples were withdrawn and, by the end of thirty minutes, isomerization to the potassium isohumulate was complete, as shown by spectral and HPLC analysis, whereas only about 8% of the requisite amount of hydrogen was consumed.

The hydrogenation of the isohumulate was continued. After six hours, hydrogenation was still not complete and was therefore allowed to run for four more hours, by the end of which time the requisite amount (two moles) of hydrogen had been consumed. This extended time period is not surprising, in view of the prior art teaching that six hours are required at 100° C. and 50 psi of pressure. (See Hay, U.S. Pat. No. 5,013,571, Column 7, line 48, Example 6.)

Since the isomerization is complete within thirty minutes, and since hydrogenation requires more than six hours, this example conclusively shows that isomerization precedes hydrogenation, and that it is the isoalpha acid which is hydrogenated under the so-called "simultaneous" conditions of Hay.

The potassium tetrahydroisohumulate made from isoalpha acids in this Example 9 were compared, as shown in Example 6, with the tetrahydroisohumulate product made by hydrogenation of alpha acids in the form of their humulates and subsequent isomerization of the tetrahydrohumulate thus produced (according to the present invention), for fruity-estery aroma. It is clear from the Example 6 Aroma Test Panel Results that the THIH product of this Example 9 did possess this undesirable aroma, whereas the latter THIH product made in Example 6 according to the present invention did not.

SUMMARY

The foregoing Examples describe the critical conditions under which tetrahydroisohumulates may be made from alpha acids, rather than from beta acids as has been done heretofore. The tetrahydroisohumulates, made by hydrogenation of alpha acids in the form of their humulates and subsequent isomerization of the resulting tetrahydrohumulates, are superior to those made by the latest existing art, which hydrogenates isoalpha acids.

The foregoing Examples and disclosure provide a novel and advantageous method for the preparation of essentially odor-free tetrahydroisohumulates (THIH) which proceeds through isomerization of the essential tetrahydrohumulate (THH) intermediate, which is in turn produced by the hydrogenation with two moles of hydrogen of a starting alkali metal humulate (H) at a pH of at least 10, the intermediate THH being thus produced with relative ease and in high yields and purity, which high yields and purity carry over to the ultimate end product, namely, to the essentially aroma-, odor-, and impurity-free THIH, which end product accordingly does not require steam-stripping or other cleanup procedure as is conventional for THIH or THIAA produced from other sources or by other procedure.

It is to be understood that the present invention is not to be limited to the exact details of operation, or to the exact compounds, compositions, methods, procedures, or embodiments shown and described, as various modifications and equivalents will be apparent to one skilled in the art, wherefore the present invention is to be limited only by the full scope which can be legally accorded to the appended claims.

We claim:

1. A process for the preparation of an alkali metal tetrahydrohumulate in high yield and purity which consists essentially of the step of hydrogenating with two moles of hydrogen and in the presence of a noble metal catalyst a solution of an alkali metal humulate at a pH of at least 10 to produce an alkali metal tetrahydrohumulate.

2. A process of claim 1 wherein the alkali metal is sodium or potassium; the solvent is a lower-alkanol, water, or a combination thereof; the pH is 10.5 to 12 and optionally buffered at such pH.

3. A process of claim 2 wherein the noble metal catalyst is palladium on charcoal.

4. A composition consisting essentially of an alkali metal tetrahydrohumulate in solution at a pH of at least 10 in the presence of a noble metal catalyst and optionally buffered at such pH.

5. A composition of claim 4 wherein the alkali metal is sodium or potassium; the solvent is a lower-alkanol, water, or a combination thereof; the pH is 10.5 to 12 and optionally buffered at such pH.

6. A process for the preparation of essentially estery or fruity odor- and aroma-free alkali metal tetrahydroisohumulate of high purity and in high yield which consists essentially of the steps of hydrogenating with two moles of hydrogen and in the presence of a noble metal catalyst a solution of an alkali metal humulate at a pH of at least 10 to produce an alkali metal tetrahydrohumulate, in accord with claim 1, and isomerizing under isomerization conditions the thus-produced alkali metal tetrahydrohumulate to form alkali metal tetrahydroisohumulate.

7. A process of claim 6 wherein the alkali metal is sodium or potassium; the solvent is a lower-alkanol, water, or a combination thereof; the pH is 10.5 to 12 and optionally buffered at such pH.

8. A process of claim 7 wherein the noble metal catalyst is palladium on charcoal.

9. A process of claim 8 wherein the isomerization is effected by boiling or catalytically using calcium or magnesium ions.

10. Essentially estery or fruity odor- and aroma-free, humulinic acid and dihydroisohumulate free metal tetrahydroisohumulate produced by the process of any one of claims 6, 7, 8, and 9.

11. A composition of claim 5 wherein the noble metal catalyst is palladium on charcoal.

* * * * *

UNITED STATES PATENT AND TRADEMARK OFFICE
CERTIFICATE OF CORRECTION

PATENT NO.  : 5,296,637

DATED       : March 22, 1994

INVENTOR(S) : Larry J. Stegink, James A. Guzinski, and Paul H. Todd, Jr.

It is certified that error appears in the above-indentified patent and that said Letters Patent is hereby corrected as shown below:

Title page, [56]; "4,007,683" should read -- 4,002,683 --.
Col. 3, line 61; "68." should read -- 68, --.
Col. 8, Table 1, line 63; insert a -- ? -- after "present".
Col. 9, Table 1-continued, line 6; insert a -- ? -- after "present".
Col. 14, line 11; insert the word -- alkali -- after "free".

Signed and Sealed this

Twenty-third Day of August, 1994

Attest:

BRUCE LEHMAN

Attesting Officer

Commissioner of Patents and Trademarks